United States Patent
Helbert et al.

(10) Patent No.: US 11,838,716 B1
(45) Date of Patent: Dec. 5, 2023

(54) HEADBAND ACCESSORY

(71) Applicant: Apple Inc., Cupertino, CA (US)

(72) Inventors: Kendall L. Helbert, San Francisco, CA (US); Benjamin C. Creed, San Francisco, CA (US); Chad J. Miller, Oakland, CA (US); Jenna L. Withrow, San Francisco, CA (US); Joshua A. Hoover, Los Gatos, CA (US); Lee M. Panecki, Los Gatos, CA (US); Donald L. Olmstead, Aptos, CA (US); Bryan A. Cloyd, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 160 days.

(21) Appl. No.: 17/319,698

(22) Filed: May 13, 2021

Related U.S. Application Data

(60) Provisional application No. 63/045,701, filed on Jun. 29, 2020.

(51) Int. Cl.
| | |
|---|---|
| *H04R 1/10* | (2006.01) |
| *A61B 5/021* | (2006.01) |
| *A61B 5/024* | (2006.01) |
| *A61B 5/0295* | (2006.01) |
| *A61B 5/00* | (2006.01) |
| *A61B 5/369* | (2021.01) |
| *A61B 5/01* | (2006.01) |

(52) U.S. Cl.
CPC ............... *H04R 1/105* (2013.01); *A61B 5/01* (2013.01); *A61B 5/021* (2013.01); *A61B 5/024* (2013.01); *A61B 5/0295* (2013.01); *A61B 5/369* (2021.01); *A61B 5/4266* (2013.01); *A61B 5/6803* (2013.01); *H04R 1/1008* (2013.01); *H04R 1/1033* (2013.01); *H04R 1/1041* (2013.01); *H04R 1/1066* (2013.01)

(58) Field of Classification Search
CPC ........ H04R 1/10; H04R 1/1008; H04R 1/105; H04R 1/1058; H04R 1/1066; H04R 1/1075; H04R 1/1091
See application file for complete search history.

(56) References Cited

U.S. PATENT DOCUMENTS

| | | | |
|---|---|---|---|
| 1,555,928 A * | 10/1925 | Morrissey | H04R 5/0335 2/209 |
| 8,098,872 B2 | 1/2012 | Chang | |
| 8,631,801 B2 | 1/2014 | Keady | |
| 9,877,101 B2 | 1/2018 | Boyajian et al. | |
| 10,188,307 B2 | 1/2019 | Henson et al. | |
| 10,455,314 B1 * | 10/2019 | Yang | H04R 1/1008 |

(Continued)

*Primary Examiner* — Kile O Blair
(74) *Attorney, Agent, or Firm* — Treyz Law Group, P.C.; G. Victor Treyz; Tianyi He

(57) ABSTRACT

An electronic device such as a pair of headphones may be configured to be worn on a head of a user. The headphones may have a headband and earcups that are coupled to the headband. The headband may have a frame and a headband frame cover that is removably attached to the frame. The cover may have protrusions, may be inflated using a pump, may include a battery and other components, and may include sensors. An earcup movement synchronization mechanism may be used to synchronize movement of a left earcup with a right earcup. A torsion spring with a stop mechanisms or other bend limiter may be configured to prevent overbending of the headband.

22 Claims, 13 Drawing Sheets

(56) References Cited

U.S. PATENT DOCUMENTS

| | | | |
|---|---|---|---|
| 10,470,708 B2 | 11/2019 | Antos et al. | |
| 2004/0264727 A1 | 12/2004 | Kim | |
| 2010/0022281 A1* | 1/2010 | Cohen | H04M 1/05 |
| | | | 455/569.1 |
| 2016/0277828 A1* | 9/2016 | Oh | H04R 1/105 |
| 2017/0374448 A1 | 12/2017 | Patel et al. | |
| 2018/0338201 A1* | 11/2018 | Mann | H04R 1/1083 |
| 2019/0222915 A1* | 7/2019 | Laurent | H04R 1/105 |

* cited by examiner

HEADBAND ACCESSORY

This application claims the benefit of provisional patent application No. 63/045,701, filed Jun. 29, 2020, which is hereby incorporated by reference herein in its entirety.

FIELD

This relates generally to electronic devices, and, more particularly, to electronic devices such as headphones.

BACKGROUND

Electronic devices such as headphones may have structures that allow the devices to be worn on the head. Speakers may be used to provide audio output.

SUMMARY

An electronic device such as a pair of headphones may be configured to be worn on a head of a user. The headphones may have a headband and earcups that are coupled to the headband.

The headband may have a frame and a cover that is removably attached to the frame. Engagement structures such as snaps, magnets, and/or other attachment mechanisms may be used in removably coupling the cover and frame.

The cover may have protrusions and other structures to enhance comfort as the headband is worn, may be adjusted using a pump that inflates the headband, may include a battery, and may include sensors and other components. The sensors may gather health information, motion information, and other information.

The earcups of the headphones may include a left earcup that is coupled to a left side of the headphones and a right earcup that is coupled to a right side of the headphones. An earcup movement synchronization mechanism in the headband may synchronize movement of the left earcup with movement of the right earcup.

A spring may be provided in the headband to bias the earcups inwardly towards the ears of a user. A torsion spring with a stop mechanism or other bend limiter may be configured to prevent overbending of the headband by the spring.

DETAILED DESCRIPTION

Electronic devices such as headphones have speakers for providing audio output to a user. Headphones may be used in systems with other equipment such as head-mounted display devices and/or may be used as stand-alone devices. In some configurations, hybrid devices may include headphone and head-mounted display components.

Figure 1:
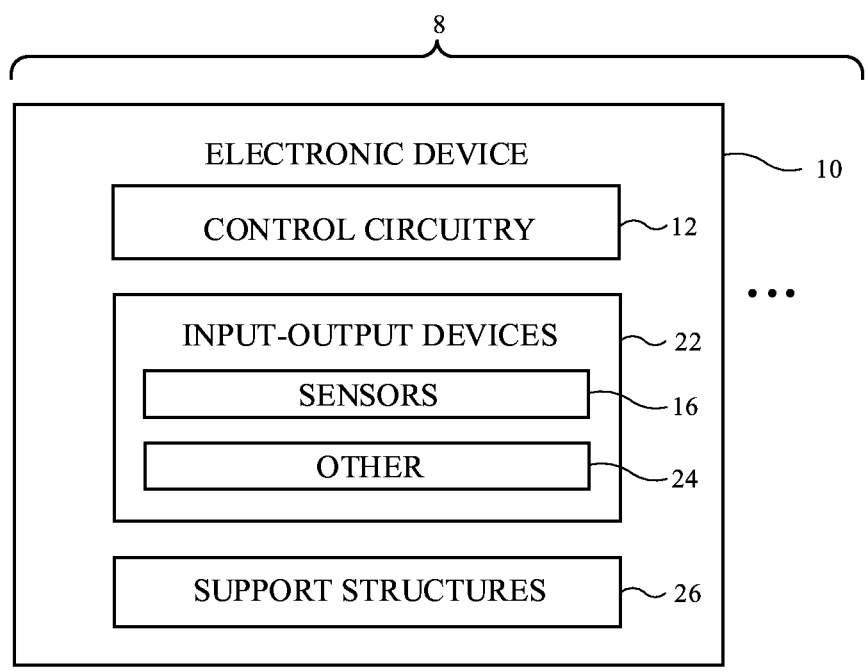
FIG. 1 is a schematic diagram of an illustrative electronic device such as a pair of headphones in accordance with an embodiment.

A schematic diagram of an illustrative system that may include one or more electronic devices is shown in FIG. 1. As shown in FIG. 1, system 8 may include one or more electronic devices such as electronic device 10. The electronic devices of system 8 may include computers, cellular telephones, head-mounted display devices, wristwatch devices, headphones, and/or other electronic devices. Configurations in which electronic device 10 is a pair of headphones may sometimes be described herein as an example.

As shown in FIG. 1, electronic devices such as electronic device 10 may have control circuitry 12. Control circuitry 12 may include storage and processing circuitry for controlling the operation of device 10. Circuitry 12 may include storage such as hard disk drive storage, nonvolatile memory (e.g., electrically-programmable-read-only memory configured to form a solid-state drive), volatile memory (e.g., static or dynamic random-access-memory), etc. Processing circuitry in control circuitry 12 may be based on one or more microprocessors, microcontrollers, digital signal processors, baseband processors, power management units, audio chips, graphics processing units, application specific integrated circuits, and other integrated circuits. Software code may be stored on storage in circuitry 12 and run on processing circuitry in circuitry 12 to implement control operations for device 10 (e.g., data gathering operations, operations involving the adjustment of the components of device 10 using control signals, etc.). Control circuitry 12 may include wired and wireless communications circuitry. For example, control circuitry 12 may include radio-frequency transceiver circuitry such as cellular telephone transceiver circuitry, wireless local area network transceiver circuitry (e.g., WiFi® circuitry), millimeter wave transceiver circuitry, and/or other wireless communications circuitry.

During operation, the communications circuitry of the devices in system 8 (e.g., the communications circuitry of control circuitry 12 of device 10), may be used to support communication between the electronic devices. For example, one electronic device may transmit video data, audio data, and/or other data to another electronic device in system 8. Electronic devices in system 8 may use wired and/or wireless communications circuitry to communicate through one or more communications networks (e.g., the internet, local area networks, etc.). The communications circuitry may be used to allow data to be received by device 10 from external equipment (e.g., a tethered computer, a portable device such as a handheld device or laptop computer, online computing equipment such as a remote server or other remote computing equipment, a head-mounted device, or other electrical equipment) and/or to provide data to external equipment.

Device 10 may include input-output devices 22. Input-output devices 22 may be used to allow a user to provide device 10 with user input. Input-output devices 22 may also be used to gather information on the environment in which device 10 is operating. Output components in devices 22 may allow device 10 to provide a user with output and may be used to communicate with external electrical equipment.

As shown in FIG. 1, input-output devices 22 may include sensors 16 and other devices 24. Sensors 16 may include, for example, three-dimensional sensors (e.g., three-dimensional image sensors such as structured light sensors that emit beams of light and that use two-dimensional digital image sensors to gather image data for three-dimensional images from light spots that are produced when a target is illuminated by the beams of light, binocular three-dimensional image sensors that gather three-dimensional images using two or more cameras in a binocular imaging arrangement, light detection and ranging sensors such as three-dimensional lidar sensors, three-dimensional radio-frequency sensors, or other sensors that gather three-dimensional image data), cameras (e.g., infrared and/or visible digital image sensors), gaze tracking sensors (e.g., a gaze tracking system based on an image sensor and, if desired, a light source that emits one or more beams of light that are tracked using the image sensor after reflecting from a user's eyes), touch sensors, capacitive proximity sensors, light-based (optical) proximity sensors, other proximity sensors, force sensors, sensors such as contact sensors based on switches, gas sensors, pressure sensors, moisture sensors, magnetic sensors, audio sensors (microphones), ambient light sensors, microphones for gathering voice commands and other audio input, sensors that are configured to gather information on motion, position, and/or orientation (e.g., accelerometers, gyroscopes, compasses, and/or inertial measurement units that include all of these sensors or a subset of one or two of these sensors), health sensors such as sensors for measuring heart rate, blood pressure, perspiration, temperature, brain wave activity, heart signals, and/or other health and/or biometric data, and/or other sensors.

User input and other information may be gathered using sensors and other input devices in input-output devices 22. If desired, input-output devices 22 may include other devices 24 such as displays, haptic output devices (e.g., vibrating components), light-emitting diodes and other light sources, speakers such as ear speakers for producing audio output, circuits for receiving wireless power, circuits for transmitting power wirelessly to other devices, batteries and other energy storage devices (e.g., capacitors), joysticks, buttons, and/or other components.

Electronic device 10 may have housing structures (e.g., housing walls, straps, headbands, etc.), as shown by illustrative support structures 26 of FIG. 1. In configurations in which electronic device 10 is a pair of headphones, support structures 26 may be head-mounted support structures that include a headband that extends in a U-shape or other suitable shape across the top of a user's head or other portion of a user's head so that the components of device 10 (e.g., speakers) are maintained at desired positions relative to the user's head (e.g., so that speakers are aligned with the user's ears). The head-mounted support structures may be configured to be worn on a head of a user during operation of device 10 and may support and enclose input-output devices 22 and control circuitry 12.

Figure 2:
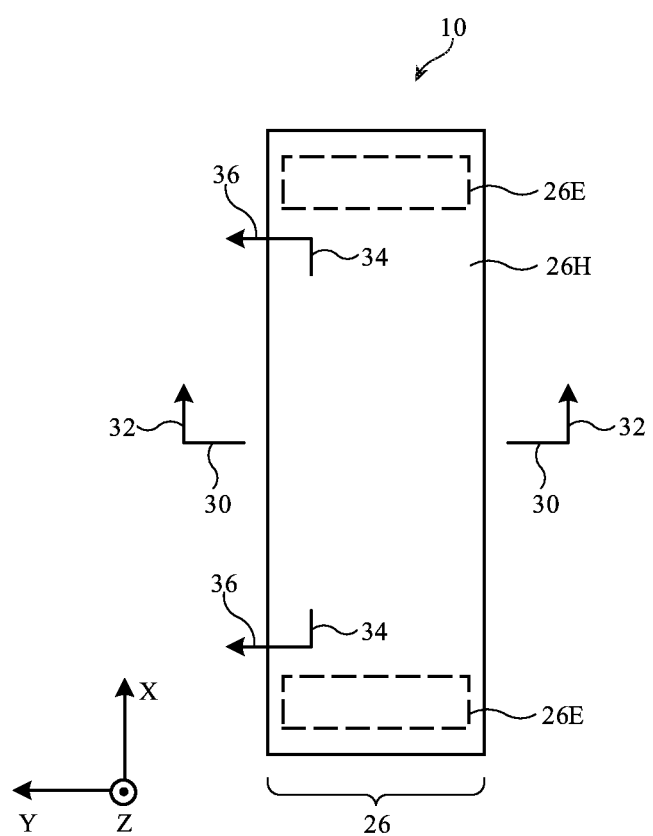
FIG. 2 is a top view of an illustrative electronic device in accordance with an embodiment.

FIG. 2 is a top view of electronic device 10 in an illustrative configuration in which electronic device 10 is a pair of headphones. As shown in FIG. 2, electronic device 10 may include head-mounted support structures 26 to house the components of device 10 and to support device 10 on a user's head. Support structures 26, which may sometimes be referred to as a support, supporting structure, head-mounted support structure, etc., may include, for example, structures that form housing walls, speaker enclosures, support members that move relative to each other, internal frame structures, and/or other structures that support and enclose the components of device 10. As shown in FIG. 2, support structures 26 may include a headband configured to be worn over the top of a user's head such as headband 26H. Support structures 26 may also include portions that enclose speakers (e.g., left and right speakers that provide sound to a user' left and right ears, respectively) such as earcups 26E.

Figure 3:
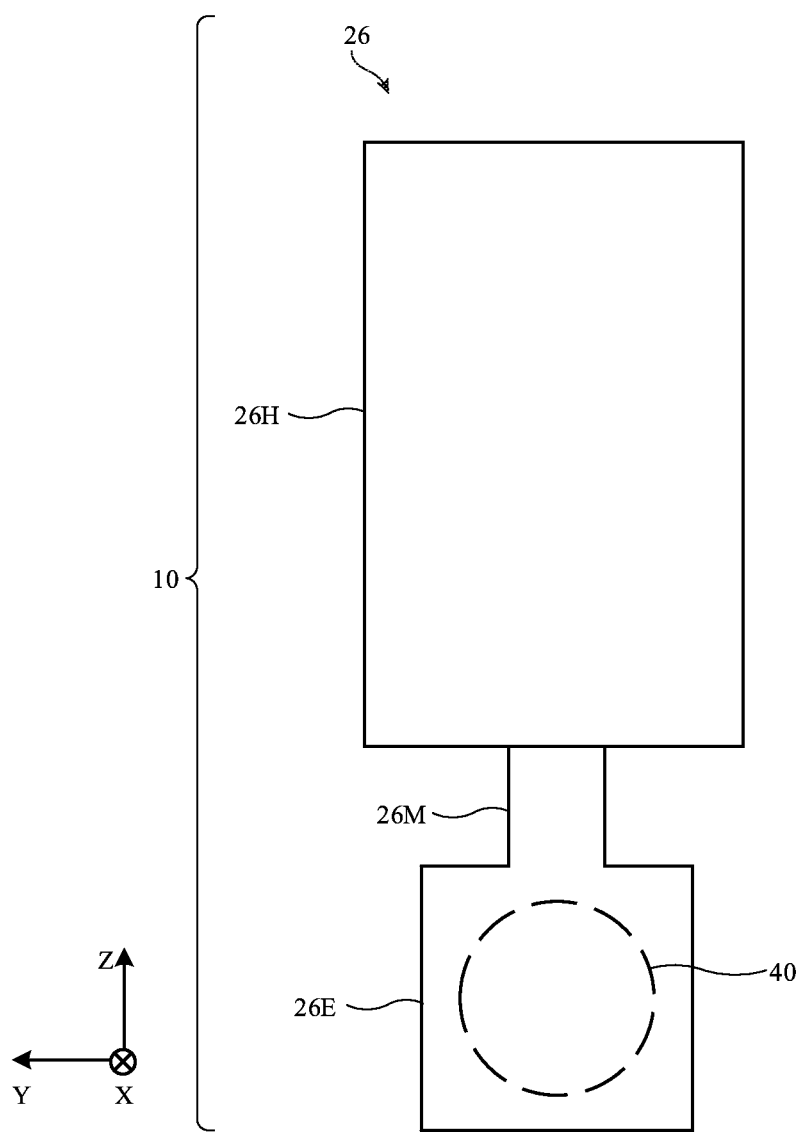
FIG. 3 is a side view of an illustrative electronic device in accordance with an embodiment.

As shown in the side view of device 10 of FIG. 3, earcups 26E may contain speakers such as speaker 40. During operation, when device 10 is being worn on a head of a user, each earcup 26E and the corresponding speaker 40 of that earcup may be aligned with a respective ear of the user. Earcups 26E may be coupled to headband 26H using support structures such as earcup support members 26M. If desired, support members 26M may be coupled to headband 26H for reciprocal motion and may be moved in and out of headband 26H to allow the size of the pair of headphones to be adjusted to accommodate different head sizes.

Figure 4:
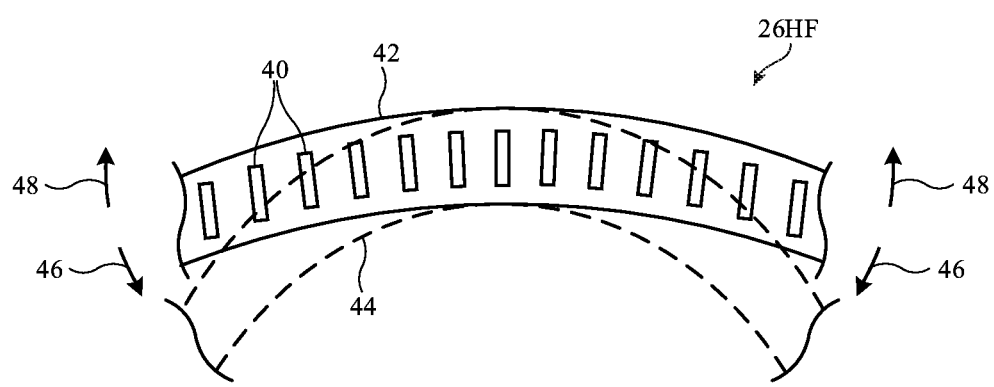
FIG. 4 is a cross-sectional view of a portion of an illustrative headband in accordance with an embodiment.

To provide headband 26H with a desired strength without adding undesired weight, headband 26H may include a frame formed from a flexible skeleton. The frame may, as an example have a series of ribs that are mounted to frame rails. FIG. 4 is a cross-sectional side view of a portion of a headband frame taken along line 34 of FIG. 2 and viewed in direction 36. As shown in FIG. 4, headband frame 26HF may have multiple ribs 40 supported by flexible rails such as rail 42. A spring may be incorporated into frame 26HF. The spring may be configured to bend frame 26HF in directions 46 towards bent position 44. When worn on a user's head, pressure from the user's head and ears will overcome the inward force of the spring and thereby push support structure 26 outwardly (e.g., frame 26HF will be bent outwardly from position 44 in directions 48). The opposing biasing force in directions 46 that is supplied by the spring may push the sides of the headband and earcups closer together, so that the headband and other structures in device 10 are held securely on the user's head.

Figure 5:
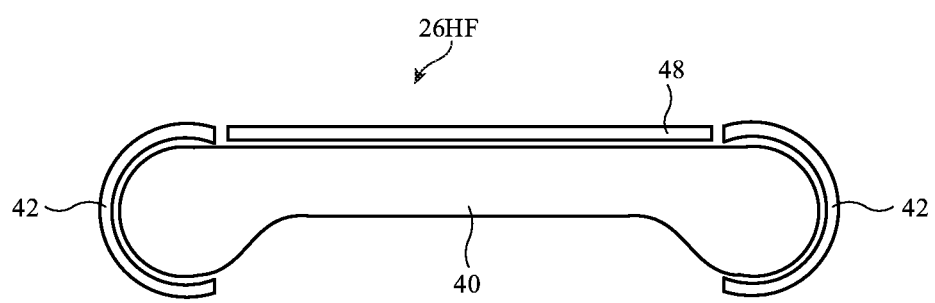
FIG. 5 is a cross-sectional view of a portion of an illustrative headband viewed along the length of the headband in accordance with an embodiment.

FIG. 5 is a cross-sectional side view of frame 26HF taken along line 30 of FIG. 2 and viewed in direction 32 of FIG. 2. As shown in FIG. 5, frame rails 42 may be configured to receive opposing ends of each rib 40. Spring 48 may extend along the length of headband frame 26HF on the top of ribs 40 between rails 42 and/or may otherwise be incorporated into frame 26HF. Spring 48 may extend along some or all of the headband frame. If desired, one or more layers of polymer or other material may be interposed between spring 48 and ribs 40 to support spring 48. Rails 42 may be formed from flexible polymer or other suitable material. Ribs 40 may be formed from polymer, metal, and/or other materials. The skeleton structures formed by rails 42 and ribs 40 may provide frame 26HF with a strong lightweight structure that is able to bend about a user's head.

Figure 6:
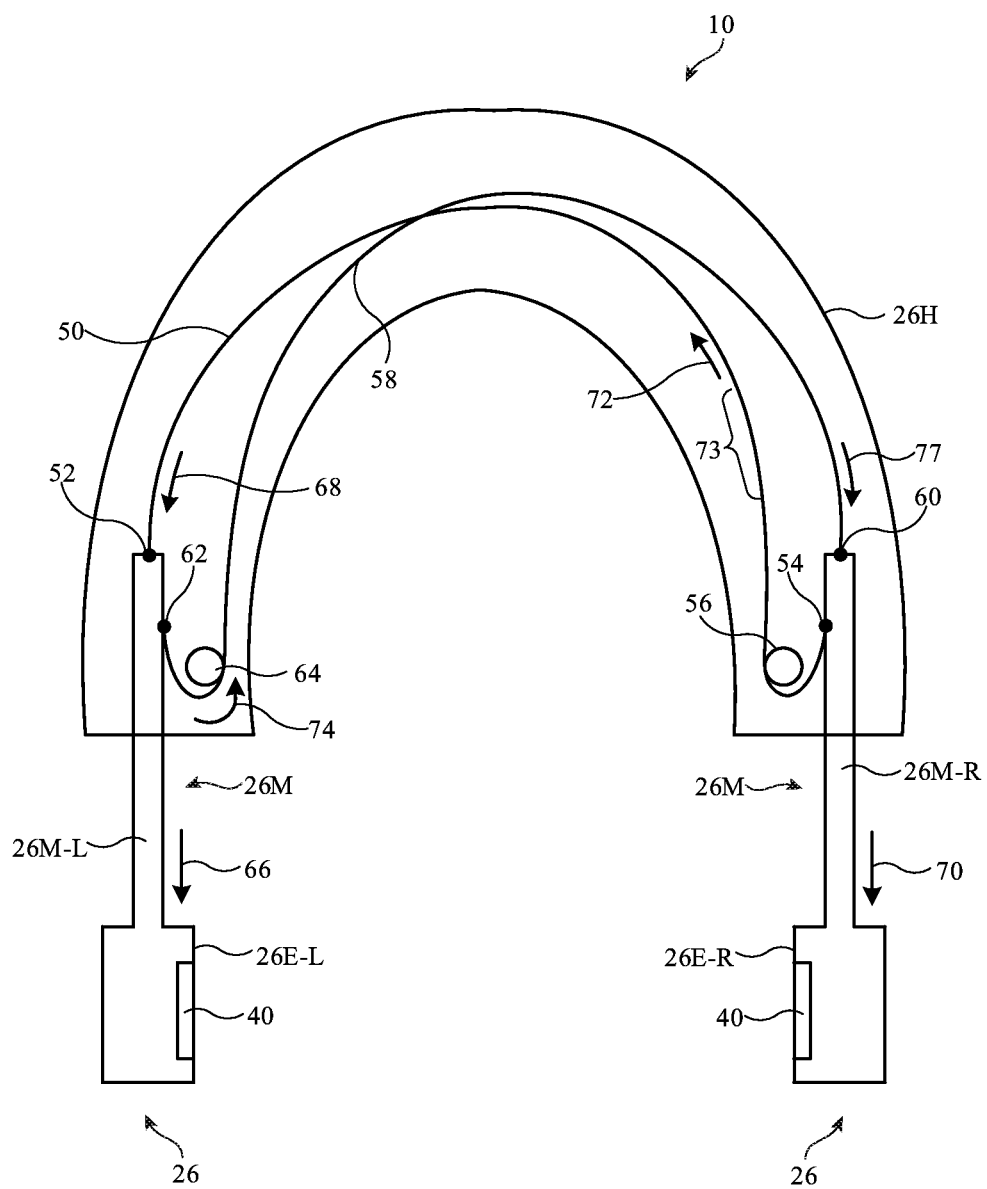
FIG. 6 is a diagram of an illustrative electronic device having an earcup movement synchronization system in accordance with an embodiment.

It may be desirable to provide the earcups of device 10 with a movement synchronization system. With this mechanism, movement by a user of the left earcup (e.g., a downward movement to expand the size of the headphones or an upward movement to reduce headphone size) will cause a corresponding movement of the right earcup (and vice versa). An illustrative earcup movement synchronization mechanism based on cables is shown in FIG. 6. Other synchronization mechanisms may be used, if desired.

In the example of FIG. 6, earcups 26E include left earcup 26E-L and right earcup 26E-R coupled to headphone headband 26H (e.g. frame 26HF in headband 26H). Earcup support members 26M include left earcup support member 26M-L and right earcup support member 26M-R. Earcup movement synchronization cables 50 and 58 are used to synchronize earcup motion. Cable 50 is attached to member 26M-L at point 52 and is attached to member 26M-R at point 54. The direction of cable 50 on the right side of headband 26H may be reversed using pulley 56. Cable 58 is attached to member 26M-R at point 60 and is attached to member 26M-L at point 62. The direction of cable 58 on the left side of headband 26H may be reversed using pulley 64. Pulleys, guiding channels, and/or other guiding structures may be provided in the middle of headband 26H to help route cables 50 and 58 and ensure that cables 50 and 58 are taught.

The earcup motion synchronization mechanism of FIG. 6 helps synchronize movement of earcups 26 on the left and right sides of the headphones. If, for example, a user pulls downwardly on left earcup 26E-L in direction 66, cable 50 on the left side of device 10 will be pulled downwardly in direction 68. This pulls cable 50 at location 73 upwardly in direction 72. Due to the operation of pulley 56, cable 50 at point 54 pulls downwardly on member 26M-R in direction 70, which moves earcup 26E-R downwardly in direction 70 by the same amount that earcup 26E-L was moved downwardly in direction 66 on the left side of device 10. During these movements, cable 58 moves in directions 74 and 77 to accommodate the synchronized movement of the left and right earcups. When earcup 26E-L is pushed upwardly, cable 58 pulls earcup 26E-R upwardly in synchronization and cable 50 moves to accommodate the synchronized movement of the earcups.

Figure 7:
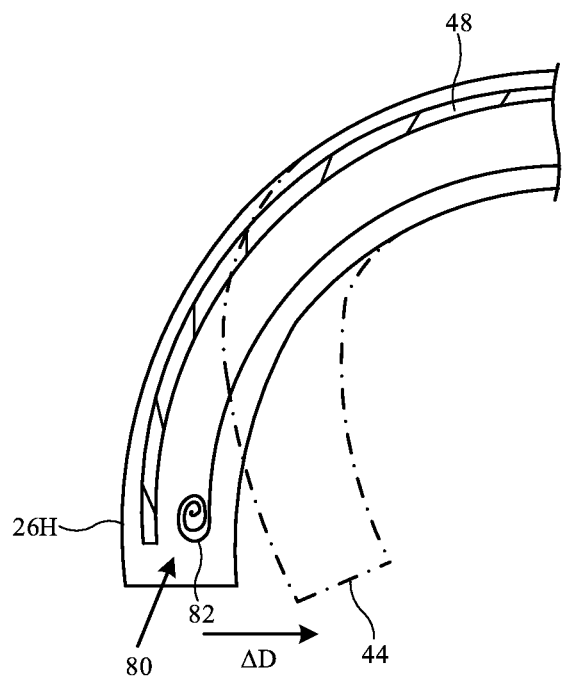
FIG. 7 is a cross-sectional view of a portion of a headband showing how the headband may be provided with a biasing structure to help provide head clamping force and a stop mechanism that serves as a bend limiter to set a minimum earcup separation and prevent overbending of the headband in accordance with an embodiment.
Figure 8:
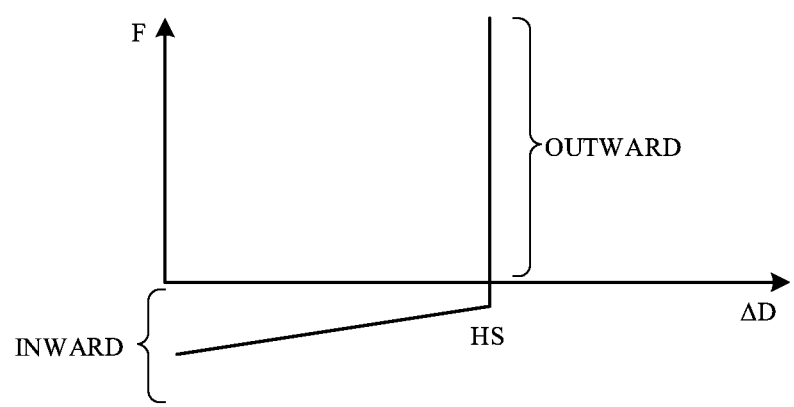
FIG. 8 is a graph showing how the illustrative biasing structure and bend limiter may impart forces on the head band while the headband is flexed by different amounts in accordance with an embodiment.

To prevent device 10 from bending inwardly more than desired due to the operation of spring 48 (FIG. 5), a tension spring clamping stop mechanism or other stop mechanism may be incorporated into device 10. This stop mechanism serves as a headband bend limiter that prevents overbending of headband 26H. As shown in FIG. 7, for example, headband 26H may include a tension spring stop mechanism such as stop mechanism 80. Mechanism 80 may include tension springs 82 on the left and/or right sides of device 10 that restrict inward motion of headband 26H. For example, spring 48 may exert a clamping force that tends to bend headband 26H inwardly towards a user in direction 46. When a predetermined amount of bending is reached, however, the limit of travel of spring(s) 82 is reached and further bending movement is prevented (e.g., headband 26H may be allowed to move distance $\Delta D$ until $\Delta D$ reaches a predefined limit so that headband 26H can bend no further inward than position 44). The graph of FIG. 8 illustrates how spring 48 may exhibit an inward bias (negative value of force F) until the value of $\Delta D$ reaches a predetermined hard stop distance HS, at which point further inward movement of the sides of headband 26H and earcups 26E towards each other is prevented.

Figure 9:
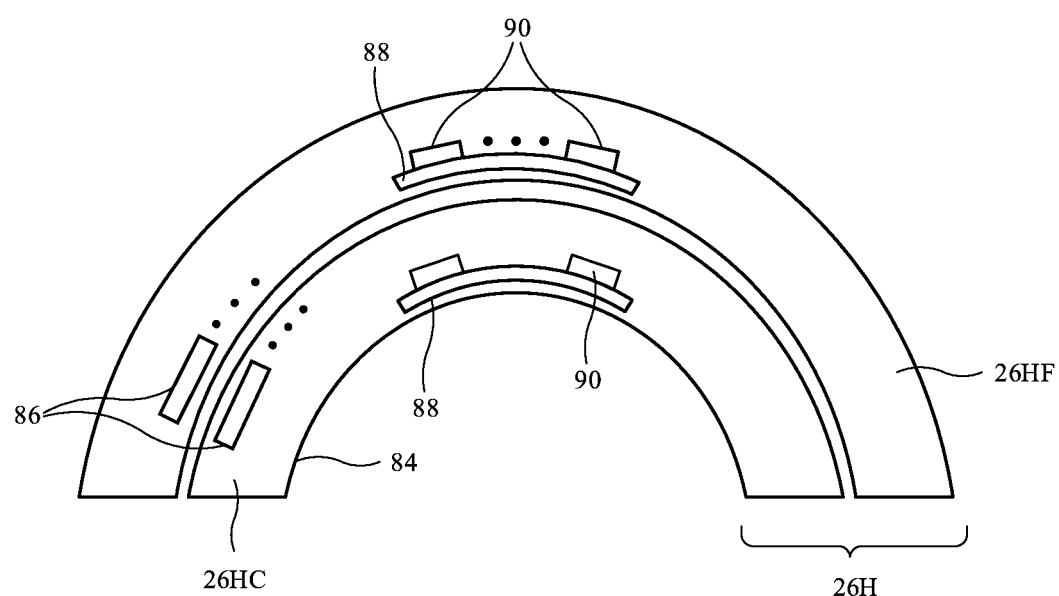
FIG. 9 is a cross-sectional side view of an illustrative headband with a frame and removable headband frame cover in accordance with an embodiment.

As shown in FIG. 9, headband 26H may include a removable cover (sometimes referred to as a removable housing member, removable headband cover, or removable headband frame cover). When headband 26H is worn on a user's head, cover 26HC may be interposed between frame 26HF and the user's head. Cover 26HC may be removably attached to the inwardly facing side of frame 26HF using magnets 86 and/or other attachment mechanisms (e.g., engagement structures such as snaps, press-fit connections, fasteners such as screws, hook-and-loop fasteners, etc.). Electrical components 90 may be mounted in the interior of frame 26FH and/or in the interior of removable cover 26HC. Components 90 may, if desired, be interconnected using signal lines in one or more printed circuits 88 or other signal paths. Components 90 may include integrated circuits, discrete components, modules, and/or other circuitry for forming control circuitry 12 and/or input-output devices 22. In an illustrative configuration, cover 26HC may contain a battery that is used to supplement a battery in frame 26HF or a battery that serves as the only battery in device 10.

Inner surface 84 of removable cover 26HC may be formed from a material that is soft to the touch (e.g., fabric, foam, etc.) so that headband 26H is comfortable to wear. Covering layers for frame 26HF and/or removable cover 26HC may, in general, be formed from polymer, metal, fabric, leather, other materials, and/or combinations of these materials. These covering layers may include rigid parts and/or strong flexible sheets that provide structural support for headband 26H and/or may include thinner cosmetic layers. Because cover 26HC is removable, cover 26HC may be replaced with a different cover (e.g. to swap batteries, to install a differently shaped cover 26HC to accommodate a different user, to allow cover 26HC to be washed, to allow a different cover 26HC with different capabilities such as a different set of sensors 16 or other input-output devices 22 to be swapped into place, etc.).

Although the configuration of FIG. 9 illustrates a mounting arrangement in which cover 26HC is attached to the inner surface of frame 26HC, different mounting arrangements may be used. For example, in an arrangement in which device 10 is a head-mounted device, removable cover 26HC may be attached to the ends of temples (e.g., in a pair of glasses) or to the inner surfaces of a helmet or pair of goggles. In arrangements in which device 10 is a sleep mask, cover 26HC may form an inner liner facing the face of a user. Wristwatches, sleep pillows, and/or other devices may also be provided with removable covers such as cover 26HC of device 10, if desired.

Figure 10:
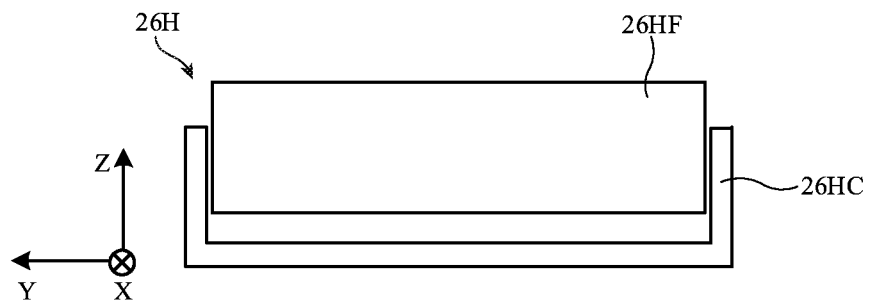
FIG. 10 is a cross-sectional view of an illustrative removable cover that has been coupled to a frame in accordance with an embodiment.
Figure 11:
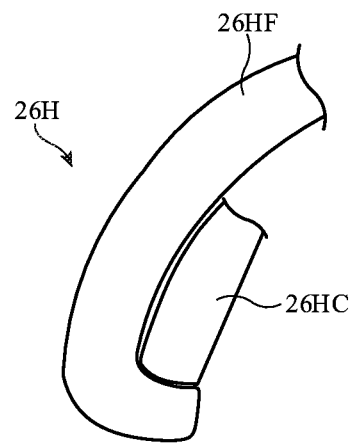
FIG. 11 is a cross-sectional view of an illustrative removable cover that is being retained by an end portion of the frame in accordance with an embodiment.

FIG. 10 is a cross-sectional side view of headband 26H in an illustrative configuration in which cover 26HC has a U-shaped cross-sectional profile configured to receive frame 26HF. In the example of FIG. 11, frame 26HF has a rounded end portion on each end of the elongated structures forming frame 26HF (e.g., on the left and right sides of device 10).

These rounded end portions receive the corresponding ends of cover 26HF. Attachment mechanisms such as these and/or other attachment mechanism may help secure cover 26HC to frame 26HF during use of device 10.

Figure 12:
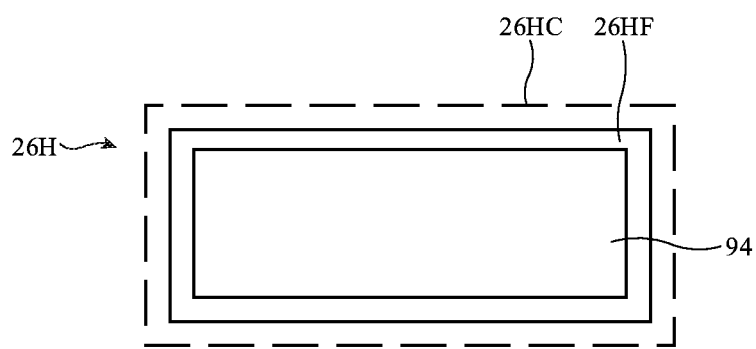
FIG. 12 is a top view of an illustrative headband with a hoop-shaped frame and removable cover in accordance with an embodiment.
Figure 13:
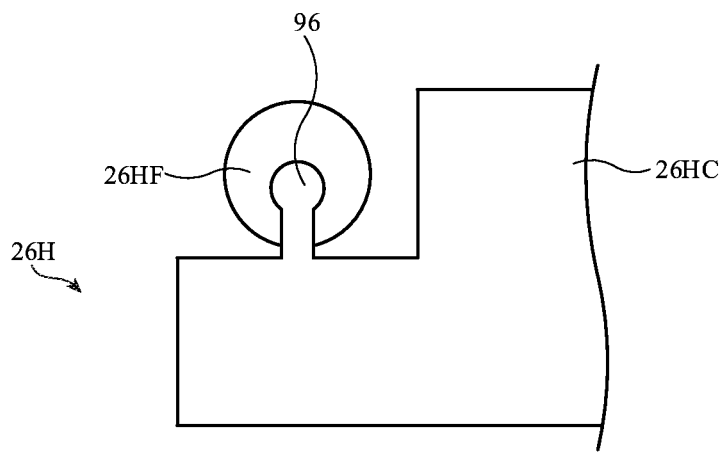
FIGS. 13 and 14 are cross-sectional views of a frame and removable cover in accordance with embodiments.
Figure 14:
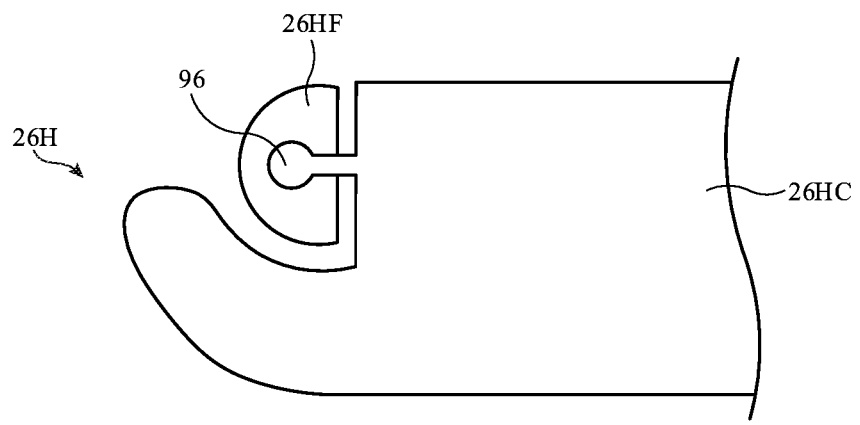

As shown in the top view of FIG. 12, frame 26HF may, if desired, have an open shape (e.g., a loop or hoop shape) in which an elongated frame member (frame member 92) surrounds central opening 94. Cover 26HC may be fixedly attached and/or removably attached to this hoop-shaped frame or other suitable frame structures. FIGS. 13 and 14 are cross-sectional side views of portions of headband 26H in illustrative configurations in which frame 26HF has a hoop shape of the type shown in FIG. 12. In these illustrative configuration, frame 26HF and cover 26HC have engagement structures such as interlocking snap structures 96 that allow cover 26HC to be removably attached to frame 26HF. In the example of FIG. 13, cover 26HC is attached to the bottom (inwardly facing) surface of frame 26HF without overlapping the side edge of frame 26HF. In the example of FIG. 14, cover 26HC has a portion that curves outwardly and at least partly covers the otherwise exposed edge of frame 26HF. Other frame and cover arrangements may be used, if desired.

Figure 15:
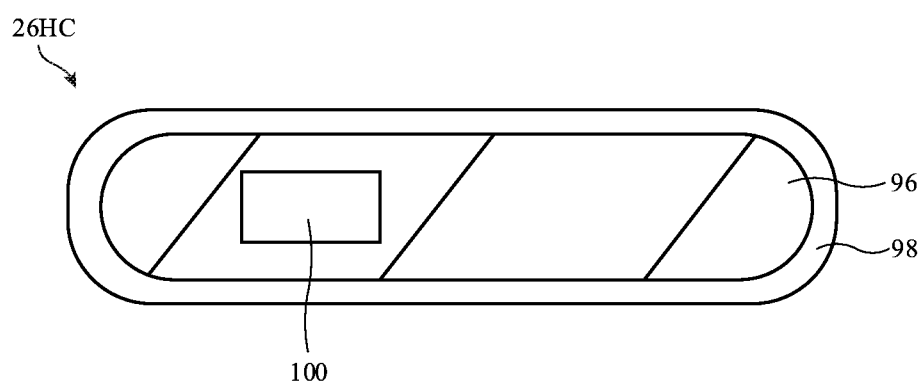
FIG. 15 is a cross-sectional side view of an illustrative removable cover in accordance with an embodiment.

As shown in FIG. 15, cover 26HC may, if desired, include a core such as core 96 and an outer covering such as covering layer 98. Core 96 may be, for example, a foam member, inflatable bladder(s), and/or other soft material. Covering layer 98 may be formed from a layer of polymer, a layer of fabric, and/or other materials (e.g. soft materials). There may be cavities in core 96 (e.g., air-filled cavities) such as cavity 100. Cavities such as cavity 100 may be placed at one or more locations in cover 26HC to adjust the softness of cover 26HC (e.g. to locally reduce stiffness and thereby increase softness of cover 26HC in portions of cover 26HC that are worn against the sides of a user's head) and/or to receive components (see, e.g., control circuitry 12 and/or input-output devices 22 of FIG. 1, which may include, for example, a battery, and/or other circuitry). Cavity 100 may, if desired, be formed from a sealed membrane wall such as a polymer bladder wall (e.g., to form a trapped air pocket).

Because cover 26HC may be formed from soft pillowy materials, cover 26HC may sometimes be referred to as a removable pillow or cover pillow. Cover 26HC may be formed from a single cover member, may be formed from two or more individual pieces, and/or may be formed from other suitable sets of one or more individual covering structures. For example, a larger central portion of cover 26HC may contain a removable battery and/or side portions of cover 26HC may include removable side members (e.g., side members without batteries).

Figure 16:
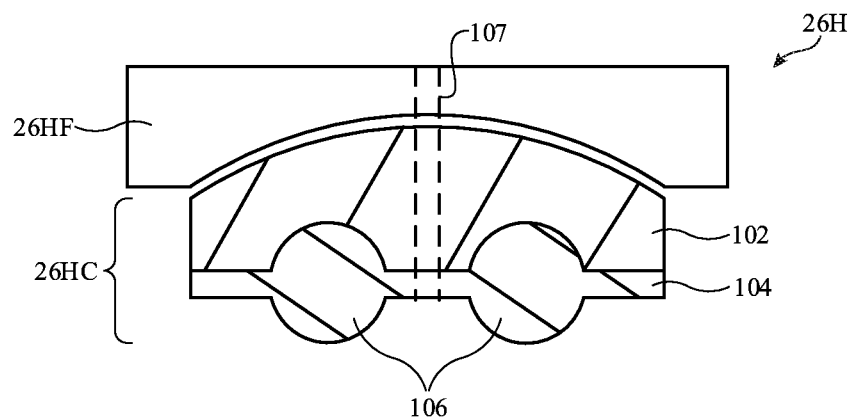
FIGS. 16 and 17 are cross-sectional side views of illustrative headband structures in accordance with embodiments.

FIG. 16 shows how cover 26HC may be formed from multiple different types of material. As shown in FIG. 16, cover 26HC may, as an example, have a first member such as member 102 that is formed from a first material (e.g., a stiff foam) and may have a second member such as member 104 that is formed from a second material (e.g. a soft foam) with different properties (e.g., a second material that is softer, more flexible, less stiff, and has a smaller elastic modulus than the first material). If desired, openings such as illustrative opening 107 (e.g., through-hole openings) may be formed vertically through frame 26HF and/or cover 26HC (e.g., to accommodate underlying components, to enhance comfort by reducing pressure hotspots and/or facilitating air flow, etc.).

Figure 17:
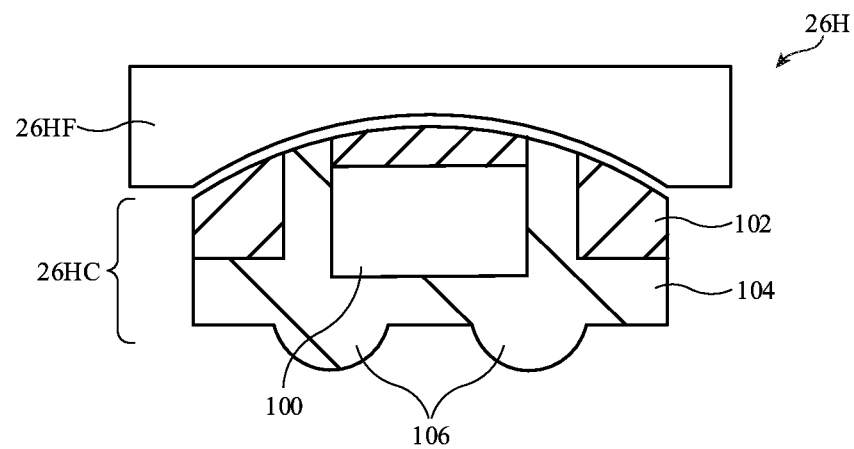

As shown in FIG. 16, member 104 may have protrusions such as protrusions 106 that face the head of the user to enhance comfort. Protrusions 106, which may sometimes be referred to as dimples may, if desired, have embedded components (e.g., sensors 16 such as force sensors for mapping various pressure points on a user's head, haptic actuators that may be adjusted in various patterns to convey information by touch to the user's head, etc.). If desired, one or more portions along the length of headband 26H may be provided with cavities such as cavity 100 of FIG. 17. The presence of cavities 100 may locally change the stiffness of headband 26H (e.g., the presence of a cavity may help locally reduce headband stiffness). The human head may, as an example, be particularly sensitive to pressure at the 12:00 position (top of the head), so placing one or more cavities 100 and/or relatively larger fractions of soft foam at the portion of headband 26HF that overlap the top-of-the-head position may help enhance comfort. Cooling liquid may, if desired, be pumped or otherwise circulated through pipes or other cavities in protrusions 106 and/or other portions of headband 26H to help cool a user's head.

Figure 18:
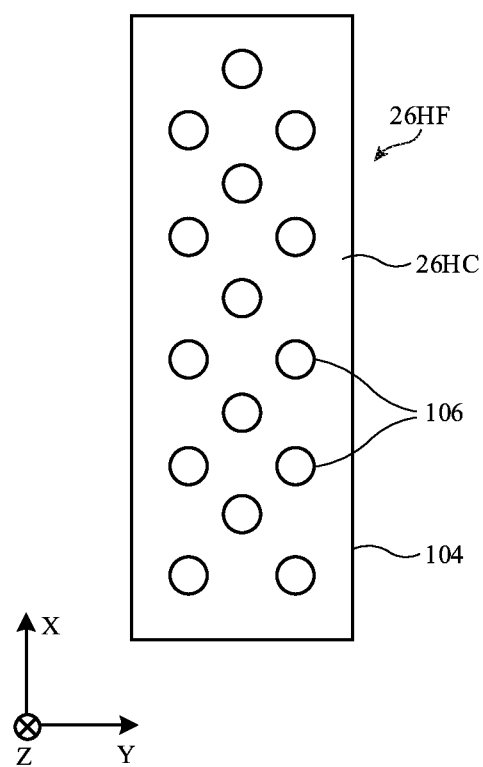
FIG. 18 is a view of a headband cover with protrusions in accordance with an embodiment.

FIG. 18 shows how cover 26HC may have protrusions 106 that extend in an array along the length of cover 26HC (e.g., along the X axis in the example of FIG. 18). Each protrusion may have a potentially different softness (elasticity) to allow sensitive areas of headband 26H to be selectively provided with enhanced softness.

Figure 19:
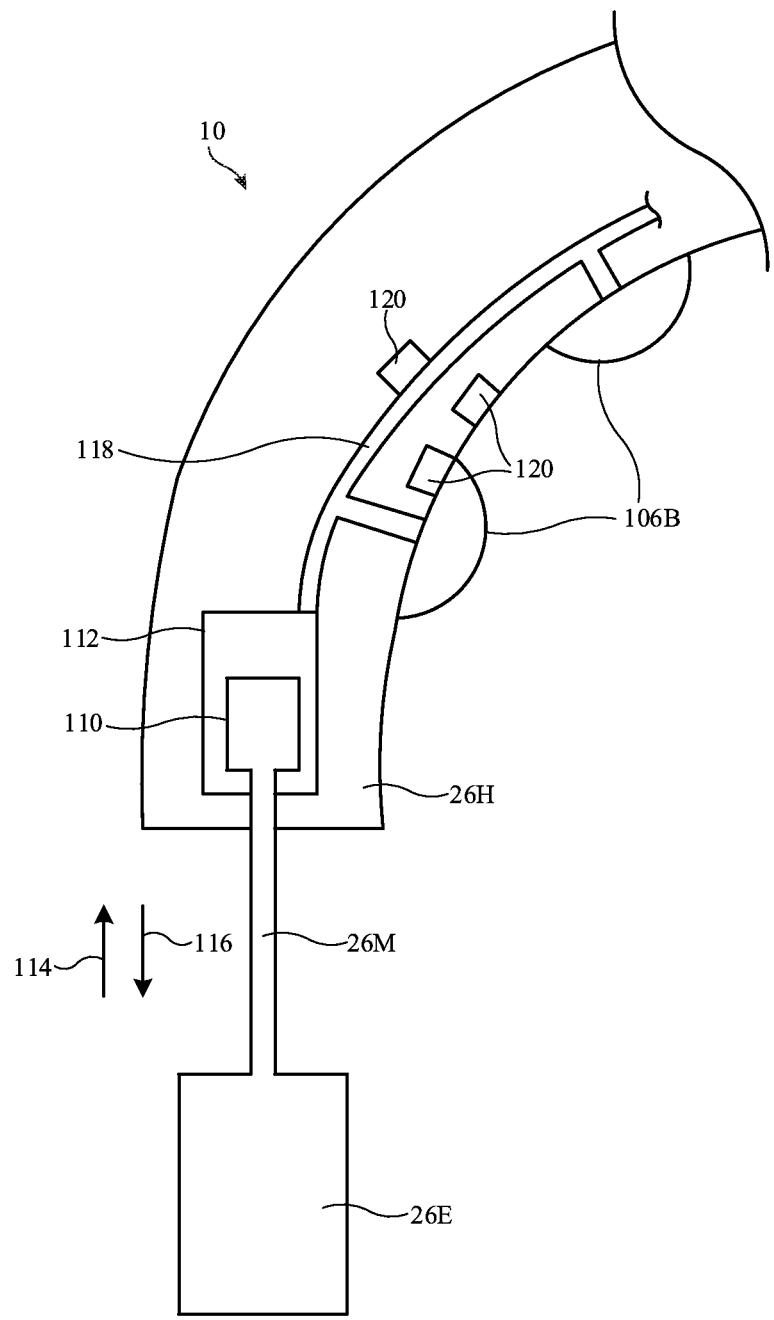
FIG. 19 is a cross-sectional side view of an illustrative headband inflation system for inflating protrusions and/or other structures in a headband in accordance with an embodiment.

The cross-sectional side view of device 10 of FIG. 19 shows how a pump may be used to fill protrusions on the inwardly facing surface of device 10 (e.g., on a removable or fixed cover) or other portions of headband 26H with fluid. As shown in FIG. 19, device 10 may have one or more pumps such as pump 112. There may be, for example, a first pump for the left side of device 10 and a second pump for the right side of device 10. Pumps such as pump 112 may be air pumps or may be configured to pump liquid or other fluid.

In the example of FIG. 19, earcup 26E is attached to earcup support member 26M. Plunger 110 of pump 112 may be coupled to member 26M, so that plunger 110 may be moved by moving (e.g., reciprocating) earcup 26E (or other portion of device 10) back and forth (e.g., up in direction 114 and down in direction 116, repeatedly). This pumping action forces environmental air or liquid from a reservoir into passageway 118 (e.g., air-filled tubing or other air passageway and/or tubing filled with other fluid) and fills bladders or other cavities in inwardly facing headband protrusions such as protrusions 106B, thereby adjusting the fit of device 10 to match a user's preference. In situations where headband 26H is inflated more than desired, pressure may be relieved using a user-actuated relief valve (as an example). If desired, pump 112 may be actuated by normal movement of the structures in device 10 (e.g., pump 112 may be actuated by the normal flexing of headband 26HF), thereby reducing or eliminating the need for a user to pump using earcup 26E. Input-output devices 22 may also include an electrically controlled pump that responds to sensor measurements or other input. For example, a sensor such as a biometric sensor in device 10 or another device in system 8 may recognize when a particular user is wearing device 10. In response, control circuitry 12 may direct the electrically adjustable pump to adjust (e.g., inflate) protrusions 106B or other portions of headband 26H and device 10 to a level that is customized to that particular user (e.g., based on sensor measurements such as pressure measurements or head size measurements or based on previously adjusted user settings).

As shown in FIG. 19, components 120 may be mounted on passageway 118, on portions of the bladders in protrusions 106B, and/or on inwardly-facing portions of head band 26HF (as examples). Components 120 may include sensors 16. For example, components 120 may include pressure sensors (e.g., a pressure sensor that measures the pressure of fluid in passageways 118), optical sensors, sensors for measuring electrical signals such as heart signals and/or brainwaves, inertial measurements units containing orientation sensors such as accelerometers, gyroscopes, and/or compasses, and/or other sensors 16. The inclusion of sensors 16 at these locations and/or other locations in device 10 allows pressure in passageway 118 and/or protrusions 106B to be measured (e.g., to measure blood pressure, to measure heart rate, to gather photoplethysmographs to assess blood volume changes, etc.) and/or allows other health-related and biometric measurements to be made (e.g., optical heart rate measurements, perspiration measurements, brainwave activity measurements such as electroencephalogram measurements, muscle activity measurements, temperature measurements, etc.). Orientation sensors may detect when a user is nodding or otherwise providing head motion input. If desired, haptic modules may be embedded in device 10 to provide directional feedback while a user is navigating the world (e.g., a tap may be provided to the left side of a user's head to direct the user to turn to the left as a user is navigating through city streets with satellite navigation assistance from device 10, etc.).

As described above, one aspect of the present technology is the gathering and use of information such as information from input-output devices. The present disclosure contemplates that in some instances, data may be gathered that includes personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, username, password, biometric information, or any other identifying or personal information.

The present disclosure recognizes that the use of such personal information, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the United States, collection of or access to certain health data may be governed by federal and/or state laws, such as the Health Insurance Portability and Accountability Act (HIPAA), whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of participation in the collection of personal information data during registration for services or anytime thereafter. In another example, users can select not to provide certain types of user data. In yet another example, users can select to limit the length of time user-specific data is maintained. In addition to providing "opt in" and "opt out" options, the present disclosure contemplates providing notifications relating to the access or use of personal information. For instance, a user may be notified upon downloading an application ("app") that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of information that may include personal information data to implement one or more various disclosed embodiments, the present disclosure also contemplates that the various embodiments can also be implemented without the need for accessing personal information data. That is, the various embodiments of the present technology are not rendered inoperable due to the lack of all or a portion of such personal information data.

The foregoing is merely illustrative and various modifications can be made to the described embodiments. The foregoing embodiments may be implemented individually or in any combination.

What is claimed is:

1. Headphones, comprising:
   a headband;

first and second earcups with speakers coupled respectively to opposing ends of the headband;
a first earcup support member configured to couple the first earcup for motion with respect to a left side of the headband;
a second earcup support member configured to couple the second earcup for motion with respect to a right side of the headband; and
an earcup movement synchronization mechanism in the headband that is configured to synchronize movement of the first and second earcups, wherein the earcup movement synchronization mechanism comprises:
a first cable having opposing ends coupled respectively to the first and second earcup support members; and
a second cable having opposing ends coupled respectively to the first and second earcup support members.

2. The headphones defined in claim 1 wherein, in response to movement of the first earcup, the first earcup support member moves into the headband by a first amount and the earcup movement synchronization mechanism moves the second earcup support member into the headband by the first amount.

3. The headphones defined in claim 1 wherein the earcup movement synchronization mechanism further comprises a first pulley that receives the first cable and a second pulley that receives the second cable.

4. The headphones defined in claim 1 wherein the headband comprise a headband frame and a cover removably coupled to the headband frame.

5. The headphones defined in claim 4 wherein the cover and the headband frame comprise magnets.

6. The headphones defined in claim 4 further comprising a pump configured to inflate the headband.

7. The headphones defined in claim 6 further comprising a spring in the headband that is configured to bias the first and second earcups towards each other.

8. The headphones defined in claim 7 further comprising a headband bend limiter configured to prevent movement of the first and second earcups towards each other more than a given amount.

9. The headphones defined in claim 1 further comprising:
a sensor in the headband.

10. Headphones, comprising:
a headband having a headband frame and a headband frame cover that is removably coupled to the headband frame, wherein the headband frame cover comprises a first foam member with a first stiffness and a second foam member with a second stiffness that is greater than the first stiffness and wherein the second foam member is interposed between the first foam member and the headband frame; and
earcups coupled respectively to opposing ends of the headband.

11. The headphones defined in claim 10 wherein the headband frame cover includes a battery.

12. The headphones defined in claim 10 wherein the headband frame cover comprises a plurality of protrusions.

13. The headphones defined in claim 10 wherein the headband frame cover has a cavity.

14. The headphones defined in claim 10 further comprising engagement structures configured to removably couple the headband frame cover to the headband frame.

15. The headphones defined in claim 10 further comprising magnets configured to removably couple the headband frame cover to the headband frame.

16. The headphones defined in claim 10 further comprising a pump configured to inflate the headband.

17. Headphones, comprising:
a headband having a headband frame and a removable cover coupled to the headband frame;
first and second earcups coupled to the headband by respective first and second earcup support members that are movable into and out of the headband, each earcup containing a respective speaker;
a bend limiter in the headband configured to prevent overbending of the headband; and
an earcup movement synchronization mechanism coupled to the first and second earcup support members to synchronize movement of the first and second earcups.

18. The headphones defined in claim 17 wherein the bend limiter comprises a torsion spring with a stop configured to prevent movement of the first earcup towards the second earcup by more than a predetermined amount.

19. The headphones defined in claim 17 wherein the earcup movement synchronization mechanism comprises first and second cables each coupled between the first and second earcup support members.

20. The headphones defined in claim 17 further comprising a battery in the removable cover.

21. The headphones defined in claim 17 further comprising a sensor selected from the group consisting of: a blood volume change sensor, a heart rate sensor, a perspiration sensor, a brainwave activity sensor, a pressure sensor, and a temperature sensor.

22. The headphones defined in claim 17 further comprising a pump configured to inflate the headband.

* * * * *

UNITED STATES PATENT AND TRADEMARK OFFICE
CERTIFICATE OF CORRECTION

| | |
|---|---|
| PATENT NO. | : 11,838,716 B1 |
| APPLICATION NO. | : 17/319698 |
| DATED | : December 5, 2023 |
| INVENTOR(S) | : Kendall L. Helbert et al. |

It is certified that error appears in the above-identified patent and that said Letters Patent is hereby corrected as shown below:

On the Title Page

Right Column, Item (57), Line 11, "mechanisms" should read -- mechanism --

In the Claims

Column 11, Line 29, "comprise" should read -- comprises --

Signed and Sealed this
Twenty-ninth Day of October, 2024

Katherine Kelly Vidal
*Director of the United States Patent and Trademark Office*